United States Patent [19]

Johnson et al.

[11] Patent Number: 5,087,783
[45] Date of Patent: Feb. 11, 1992

[54] TRANSALKYLATION OF BENZENE IN A MOVING BED

[75] Inventors: Roger C. Johnson; Daniel McCarthy, both of Randolph; Andrei Rhoe, Wyckoff, all of N.J.

[73] Assignee: Lummus Crest, Inc., Bloomfield, N.J.

[21] Appl. No.: 610,950

[22] Filed: Nov. 9, 1990

Related U.S. Application Data

[62] Division of Ser. No. 186,959, Apr. 27, 1988, Pat. No. 4,973,780.

[51] Int. Cl.$^5$ .................. C07C 5/22; C07C 15/12; B01J 20/34
[52] U.S. Cl. .................. 585/475; 585/474; 585/470; 502/38; 502/52
[58] Field of Search .................. 585/470, 474, 475; 502/38, 52

[56] References Cited

U.S. PATENT DOCUMENTS 4,237,329  12/1980  Kamiyama et al. .................. 585/474
4,885,426  12/1989  Chu et al. .................. 585/475

FOREIGN PATENT DOCUMENTS 8912613  12/1989  PCT Int'l Appl. .................. 585/474

OTHER PUBLICATIONS

Kirk-Othmer *Encyclopedia of Chemical Technology*, 3rd ed., vol. 19, John Wiley & Sons (1982), p. 886.

*Primary Examiner*—Anthony McFarlane
*Assistant Examiner*—Nhat Phan
*Attorney, Agent, or Firm*—Elliot M. Olstein; Susan A. Capello

[57] ABSTRACT

An improved process for the alkylation of benzene in the presence of an alkylation catalyst. The catalyst bed may be caused to move in a direction countercurrent to the movement of the benzene and olefin, or a portion of the catalyst bed is periodically removed and replaced. A regeneration step, whereby the catalyst is heated in a controlled oxygen atmosphere in order to reactivate the catalyst, is also described.

7 Claims, 1 Drawing Sheet

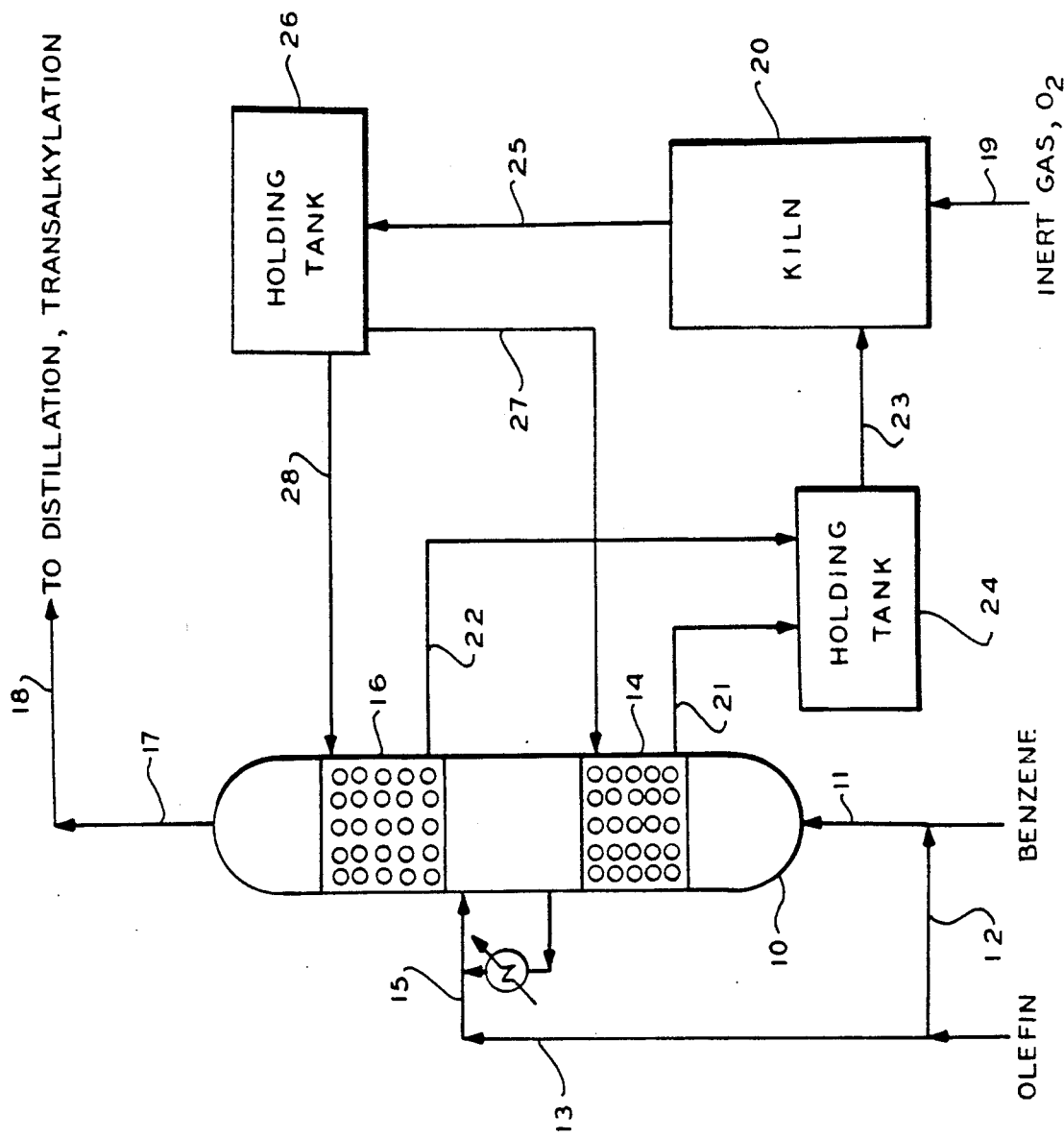

TRANSALKYLATION OF BENZENE IN A MOVING BED

This is a division of application Ser. No. 186,959, filed Apr. 27, 1988 now U.S. Pat. No. 4,973,780.

This invention relates to a process wherein benzene is alkylated with an olefin in the presence of an alkylation catalyst in order to produce alkylbenzenes.

In the prior art, it has been known to effect alkylation of benzene with olefin in an alkylation reactor in the presence of a catalyst, such as zeolite catalyst. The alkylation catalyst is maintained as one or more fixed beds in the alkylation reactor. The effluent from the alkylation reactor is then distilled and/or flashed to recover a desired alkylbenzene product as well as other products such as paraffins, benzene, polyalkylbenzenes, or diphenylalkanes which may be produced. Benzene and/or polyalkylbenzenes may, if desired, be recycled to the alkylation reactor or may be passed to a transalkylator wherein benzene and polyalkyl benzenes are passed over a transalkylation catalyst bed to form additional alkylbenzenes. The transalkylator effluent may be distilled in a manner the same as or similar to the distillation of the alkylation reactor effluent.

SUMMARY OF THE INVENTION

Applicants' invention is an improvement in a process wherein a feed of benzene is alkylated with an olefin in an alkylation reactor in the presence of an alkylation catalyst. The alkylation reactor, or alkylator, has at least one stage. In accordance with the present invention, a portion of the catalyst bed is replaced on a continuous or periodic basis. In accordance with an aspect of the present invention, alkylation of benzene with olefin is effected in the presence of a moving bed of alkylation catalyst, i.e., a portion of the catalyst is continuously replaced. In a preferred embodiment, the alkylation catalyst bed is caused to move countercurrently with respect to the olefin and benzene feed. The alkylation catalyst may be a zeolite catalyst. The olefin is preferably selected from the class consisting of ethylene and propylene, which, when used to alkylate benzene, produce ethylbenzene or cumene product, respectively.

If there is more than one catalyst bed (two or more stages) the catalyst is preferably replaced in each stage or bed separately. In accordance with another aspect of the present invention, a portion of the catalyst in the bed is periodically replaced by removing a layer of catalyst from the bed and adding a layer of catalyst to the bed. The catalyst layer which is removed is preferably comprised of deactivated catalyst and the added layer is active catalyst. In accordance with a preferred embodiment, catalyst is removed from the bottom of the bed, and catalyst is added to the top of the bed. As an alternative process, removal of a portion of the catalyst from the top of the bed may take place and new, regenerated or fresh catalyst may be added to the bottom of the bed, when the alkylator feed is introduced at the top of the bed and travels to the bottom of the bed.

In the alkylator, olefin and benzene are preferably introduced into the bottom of the bed and it is preferred to remove a portion of the catalyst from the bottom of the stage or bed and replace it with new catalyst at the top of the stage or bed because during alkylation, the catalyst becomes inactivated in layers from the bottom up to the top, thus forming strata of inactive catalyst.

The effluent from the alkylator may be flashed and/or distilled to recover products such as paraffins, benzene, polyalkylbenzene, and diphenylalkanes, as well as the desired alkylbenzenes. Benzene and distilled polyalkylbenzenes may be sent to a transalkylator in order to be reacted in the presence of an alkylation catalyst to form alkylbenzenes. The alkylation catalyst in the transalkylator may be a moving bed of catalyst as described above. Diphenylalkanes can be sent to a diphenylalkane converter where they are converted to alkylbenzenes in the presence of an alkylation catalyst, which may be a moving bed of alkylation catalyst as described above. In both the transalkylator and the diphenylalkane converter, the bed of catalyst need not move in a direction countercurrent to the direction of the feed to the transalkylator or diphenylalkane converter because there are no strata of inactivation of the alkylation catalyst in the transalkylator or diphenylalkane converter. In addition, in both the transalkylator and diphenylalkane converter, a portion of the catalyst bed may be periodically replaced by removing a layer of catalyst from the bed and adding a layer of catalyst to the bed as described above.

When a portion of inactivated catalyst is removed from a bed or stage of the alkylator, it is then passed to a catalyst regeneration zone. The catalyst regeneration zone may be "off site", i.e., separate from the alkylation apparatus, or it may be part of a closed loop system with an alkylator, a transalkylator, or a diphenylalkane converter. In the catalyst regeneration zone, carbonanceous materials such as tar, coke, and other hydrocarbons are burned off in a controlled $O_2$ atmosphere. This process preferably results in a slow combustion of the materials in the regeneration zone without the creation of "hot spots". Preferred temperatures for the catalyst regeneration zone are from about 400° C. to about 500° C. In the catalyst regeneration zone, the $O_2$ content may initially be at about 0.5%, followed by an increase in the $O_2$ content to about 2%. The inactivated catalyst is preferably heated for a period from about 8 hours to about 24 hours.

The regeneration of the catalyst can be a batch regeneration wherein inactivated catalyst is removed from the alkylator, passed to a first holding tank and held until the holding tank is filled with catalyst. The catalyst is then passed to the regeneration zone, regenerated, and then passed to a second holding tank. When new, regenerated, catalyst is needed, the regenerated catalyst can be passed from the second holding tank to the alkylator, where the regenerated catalyst again becomes part of the catalyst bed.

In an embodiment where a catalyst portion is periodically replaced, the amount of inactivated catalyst which is periodically removed preferably may be from about ¼ to about ⅓ of the total amount of catalyst in the bed. There is usually from about 3 feet to about 10 feet of catalyst in the bed. Thus, the period of time between replacements of portions of catalyst is determined by how long it takes to inactivate the portion of catalyst.

The temperature of the catalyst bed may be monitored in order to determine where temperature increases occur in the catalyst bed. In a portion of the catalyst bed that is deactivated, no sharp increases in temperature of this portion of the catalyst bed will be detected during alkylation.

The use of a moving catalyst bed, or a bed where a layer of catlyst is periodically replaced, decreases the amount of coking in the alkylation reactor, which helps to prevent catalyst deactivation. A replacement of catalyst (periodically or continuously) allows for a decrease in the volume of catalyst necessary for the alkylation of benzene and, therefore, a smaller alkylation reactor may be used. In addition, replacement of catalyst (periodically or continuously) permits the use of a ratio of benzene to olefin lower than that used in prior art, fixed bed alkylators. The use of a catalyst regeneration zone enables one to regenerate deactivated catalyst and recycle the catalyst to the alkylation reactor, which lessens the need for reactor shutdown and bulk replacement of spent catalyst.

The invention will be described with reference to the accompanying drawings, wherein:

BRIEF DESCRIPTION OF THE DRAWING

The drawing is a simplified schematic representation of an embodiment of the alkylation process of the present invention.

DETAILED DESCRIPTION OF THE INVENTION

Referring now to the drawing, benzene is introduced into alkylator 10 through line 11 and is passed to stage 14 of alkylator 10. In the embodiment shown, alkylator 10 contains two reaction stages 14 and 16. In accordance with the invention, however, any number of reaction stages may be contained within alkylator 10. Although the embodiment shown depicts benzene as being introduced into only one stage of alkylator 10, benzene may be introduced directly into each stage of alkylator 10 as well.

Olefin may be passed through lines 12 and 11 for introduction into stage 14 of alkylator 10, as well as being passed through lines 13 and 15 for introduction into stage 16 of alkylator 10. Any olefin may be used in accordance with this invention, although ethylene and propylene are preferred. Overall benzene to olefin mole ratios may be from about 2:1 to about 20:1, preferably at about 3:1 to about 9:1.

Contained within each of stages 14 and 16 of alkylator 10 is a bed of alkylation catalyst. The bed may be a continuously moving bed of catalyst wherein a portion of catalyst is continuously replaced, or a layer of catalyst may be periodically replaced by removing a layer of catalyst from the bed and adding a layer of catalyst to the bed. In a preferred embodiment, the alkylation catalyst is a zeolite catalyst. Preferred zeolite catalysts are zeolite X, zeolite Y, zeolite L, zeolite Beta, ZSM-5, Omega crystal zeolites, mordenite, and chabazite. The benzene and olefin introduced into stage 14 of alkylator 10 is then converted to alkylbenzene under the following catalytic conversion conditions:

|  | Broad range | Preferred range |
| --- | --- | --- |
| outlet temp (°F.) |  | 150–900  200–600 |
| Pressure (psig) |  | 150–2,000  250–1,000 |
| Space Velocity (LHSV) | 2–1,000 | 4–100 |

The feed from stage 14 of alkylator 10 is then passed to stage 16 of alkylator 10, into which olefin from line 15 is also introduced. Unreacted benzene and olefin from stage 14 and olefin from line 15 are then reacted in stage 16.

Preferably, each reaction stage is adiabatic and the outlet temperature of stage 16 does not exceed the outlet temperature of stage 14. In reactors having more than two stages, the outlet temperature of each reactor stage preferably does not exceed the outlet temperature of the preceding stage. In another embodiment, the increase in temperature in each stage of the alkylator 10 does not exceed 100° F., preferably not exceeding 75° F. In addition, cooling of the effluent may occur between the stages of alkylator 10.

In a preferred embodiment the beds contained within stages 14 and 16 of alkylator 10 are continuously moving beds which are caused to move in a direction countercurrent to the movement or flow of benzene and olefin in stages 14 and 16. This countercurrent movement is an aid in the prevention of early deactivation of the catalyst by preventing undesired coking in the alkylator reaction stages.

The temperature of each bed or stage of catalyst is monitored in order to determine where temperature increases occur in order to determine catalyst activity. If a portion of the catalyst has become deactivated, no sharp temperature increases will occur in that portion. A deactivated portion of catalyst can then be removed from stage 14 through line 21 and/or from stage 16 through line 22, and passed to holding tank 24. Catalyst can be removed from stages 14 and/or 16 continuously. Preferably, it is a bottom portion of the catalyst that is continuously removed. Periodically, inactivated catalyst is passed from holding tank 24 through line 23 to kiln 20. In another embodiment, a layer of catalyst, e.g., a bottom layer of the catalyst bed, in stages 14 and/or 16 is periodically withdrawn and passed to the holding tank 24, and subsequently passed to the kiln 20. The period of time between withdrawals of a layer of catalyst from stages 14 and/or 16 is determined by how long it takes for the layer to become deactivated.

During regeneration of the catalyst in kiln 20, carbonaceous materials such as tar, coke, and other hydrocarbons are burned off in a controlled oxygen atmosphere. The catalyst is oxidized with molecular oxygen generally provided in admixture with an inert gas introduced through line 19 into kiln 20. The inert gas has a low concetration of $O_2$, e.g., about 0.5% $O_2$, which can be increased to about 2%. The catalyst is heated in the kiln 20 at a temperature of preferably from about 400° C. to about 500° C. and for a period of from about 8 hours to about 24 hours.

After the catalyst has been regenerated in kiln 20, it is passed through line 25 to holding tank 26. The regenerated catalyst remains in holding tank 26 until new, regenerated catalyst is needed in stage 14 or stage 16 of alkylator 10. When regenerated catalyst is needed in alkylator 10, it can be passed from holding tank 26 through line 27 to stage 14, and/or from holding tank 26 through line 28 to stage 16. Preferably, the catalyst is passed from holding tank 26 through line 27 to stage 14, and/or from holding tank 26 through line 28 to stage 16 continously. Alternatively, the regenerated catalyst is passed to stages 14 and/or 16 periodically. As shown, it is seen that the regenerated catalyst, in a preferred embodiment, is added to the top of stages 14 and/or 16. The catalyst, in the preferred embodiment, is withdrawn from the bottom of the stages 14 and 16 of alkylator 10 because the catalyst, in the embodiment shown, becomes inactivated in strata from the bottom to the top of each stage. In alternative embodiments, the catalyst may be withdrawn from the top of stages 14 and/or 16 of alkylator 10, and new, regenerated catalyst may be added to the bottom of stages 14 and/or 16 of alkylator 10.

The regeneration zone comprising holding tank 24, line 23, kiln 20, line 25, and holding tank 26, may be part of a closed loop system which includes alkylator 10, or the regeneration of the catalyst may be done off-site, wherein the regeneration zone is not part of a closed loop system. When a continously moving bed is used, holding tank 24, line 23, kiln 20, line 25, and holding tank 26 must be part of a closed loop system. When the regeneration zone is not part of a closed loop system, holding tank 24 is taken off-site upon being filled with inactivated catalyst. This inactivated catalyst is then passed to an off-site kiln where regeneration of the catalyst takes place as described above. The regenerated catalyst is then passed from the kiln to another holding tank, which may be connected with line 27 to stage 14 and with line 28 to stage 16 when new, regenerated catalyst is needed in stages 14 and/or 16 of alkylator 10.

Effluent from stage 16 of alkylator 10 is passed through lines 17 and 18 for further processing. The effluent may be flashed and/or distilled to recover products such as paraffins, benzene, alkylbenzene, polyalkylbenzene, and diphenylalkanes. Benzene may be recycled to alkylator 10, or may be passed to a transalkylator (not shown), whereby benzene and distilled polyalkylbenzenes are reacted under catalytic conversion conditions to form alkylbenzenes. Polyalkylbenzenes may also be recycled to alkylator 10 in some instances. Transalkylation may take place in the presence of at least one continuously moving bed of transalkylation catalyst, or in the presence of at least one catalyst bed wherein a layer of catalyst is periodically removed and a replacement layer is added. Transalkylation may take place at a temperature from about 150° F. to about 900° F., at a pressure from about 150 psig to about 2,000 psig, at a total LHSV from about 1 to about 1,000, and wherein the feed to the transalkylator has a phenyl to alkyl group ratio from about 2 to about 50. Diphenylalkanes may be passed to a diphenylalkane converter (not shown). Diphenylalkane conversion may take place at a temperature from about 350° F. to about 800° F., and the residence time may be from about 5 minutes to about 80 minutes. This converter may contain one or more moving catalyst beds as well, or one or more catalyst beds wherein a layer of catalyst is periodically removed and a replacement layer is added. Preferred alkylbenzenes formed in alkylator 10 and in the transalkylator are ethylbenzene and cumene.

When a moving bed is used in a transalkylator or in a diphenylalkane converter, the moving bed need not move in a direction countercurrent to the direction of movement of the feed to the transalkylator or diphenylalkane converter. This is because there are no strata of deactivation of the catalyst in the transalkylator or in the diphenylalkane converter. In other respects, however, portions of catalyst may be withdrawn from and replaced in the transalkylator or in the diphenylalkane converter as described above for the continuous withdrawal from stages 14 and/or 16, regeneration in kiln 20, and continuous replacement of catalyst in stages 14 and/or 16 of alkylator 10.

As an alternative to a moving bed wherein a portion of catalyst is removed continuously, a bed of catalyst may be used wherein periodically a layer of deactivated catalyst is being removed from a stage of alkylator 10, or a transalkylator or diphenylalkane converter, and a new layer of regenerated catalyst is added to the stage or bed. Preferably, the deactivated catalyst layer is withdrawn from the bottom of each stage, and the new regenerated layer of catalyst is added to the top of each stage, although a layer of catalyst can be withdrawn from the top of each stage and a new, regenerated catalyst layer can be added at the bottom of each stage or bed.

Advantages of the present invention include the reduction of coking in the reactor and the prevention of total catalyst deactivation and the consequent requirement for plant shutdown and replacement of the deactivated catalyst with new or regenerated catalyst. When a portion of the catalyst eventually does become deactivated, it may be passed to the kiln wherein the catalyst is regenerated via an appropriate procedure such as by passing a heated mixture of inert gas and molecular oxygen over the catalyst, and then the catalyst may be recycled to the alkylator. The moving catalyst bed also enables one to use a feed to the alkylator having a lower benzene to olefin ratio and also decreases the volume and amount of catalyst necessary for the alkylation reactions. This, in turn, enables one to use a smaller reactor for carrying out the alkylation reactions.

It is to be understood, however, that the scope of the invention is not to be limited to the specific embodiments described above. For example, alkylation catalysts other than zeolites may be employed, and the reactor may contain any number of stages. A regeneration apparatus other than a kiln may also be used. The invention may be practiced other than as particularly described and still be within the scope of the accompanying claims.

What is claimed is:

1. A process for transalkylating benzene with polyalkylbenzene in a transalkylation reactor containing at least one bed of transalkylation catalyst, comprising:
    introducing a feed of benzene and polyalkylbenzene at a first end of said bed;
    monitoring the temperature of said bed to determine deactivated portions of said bed;
    removing an inactive portion of said catalyst from the first end of said bed based on said monitoring of temperature of said bed; and
    adding an active portion of said catalyst to a second end of said bed, said second end being an end opposite to said first end of said bed.

2. The process of claim 1 wherein said transalkylation catalyst is a zeolite catalyst.

3. The process of claim 1 wherein said inactive portion of said catalyst is continuously removed from said bed and said active portion of said catalyst is continuously added to said bed.

4. The process of claim 1 wherein said inactive portion of said catalyst is periodically removed from said bed and said active portion of said catalyst is periodically added to said bed.

5. The process of claim 1 wherein said removing of said inactive portion of said catalyst from said bed comprises:
    passing said inactive portion of said catalyst to a holding means;
    passing said inactive portion from said holding means to a catalyst regeneration means; and
    regenerating said inactive portion of said catalyst.

6. The process of claim 5 wherein said regeneration of said inactive portion of said catalyst comprises:

oxidizing said inactive portion of said catalyst with an atmosphere initially comprising about 0.5% molecular oxygen in admixture with an inert gas; and increasing said molecular oxygen content to about 2% during said regeneration.

7. The process of claim 5 wherein said adding of said active portion of catalyst to said catalyst bed comprises:
passing said active portion of catalyst from a catalyst regeneration means to a holding means; and
passing said active portion of catalyst from said holding means to said catalyst bed.

* * * * *